(12) United States Patent
Bracewell et al.

(10) Patent No.: US 10,344,051 B2
(45) Date of Patent: *Jul. 9, 2019

(54) CHROMATOGRAPHY MEDIUM

(71) Applicant: Puridify Ltd., Hertfordshire (GB)

(72) Inventors: Daniel Gilbert Bracewell, London (GB); Robert Stevens, London (GB); Oliver Hardick, London (GB)

(73) Assignee: Puridify Ltd., Stevanage (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/714,781

(22) Filed: Sep. 25, 2017

(65) Prior Publication Data

US 2018/0094022 A1 Apr. 5, 2018

Related U.S. Application Data

(63) Continuation of application No. 14/356,817, filed as application No. PCT/GB2012/052768 on Nov. 7, 2012, now Pat. No. 9,802,979.

(30) Foreign Application Priority Data

Nov. 7, 2011 (GB) .................................. 1119192.1

(51) Int. Cl.
*C07K 1/16* (2006.01)
*B01D 15/36* (2006.01)
(Continued)

(52) U.S. Cl.
CPC ............ *C07K 1/16* (2013.01); *B01D 15/1821* (2013.01); *B01D 15/361* (2013.01);
(Continued)

(58) Field of Classification Search
None
See application file for complete search history.

(56) References Cited

U.S. PATENT DOCUMENTS 5,863,428 A * 1/1999 Ma .................... B01D 15/22
210/198.2
6,790,528 B2 9/2004 Wendorff et al.
(Continued)

FOREIGN PATENT DOCUMENTS

DE 19629208 A1 1/1998
EP 1614795 A1 1/2006
(Continued)

OTHER PUBLICATIONS

Zhang et al, "Fabrication and bioseparation Studies of Adsorptive Membranes/Felts Made From Electrospun Cellulose Acetate Nanofibres", Journal of Membrane Science, No. 319, 2008, pp. 176-184.*

(Continued)

*Primary Examiner* — Peter D. Mulcahy
(74) *Attorney, Agent, or Firm* — Eversheds Sutherland (US) LLP

(57) ABSTRACT

The present invention provides a chromatography medium comprising one or more electrospun polymer nanofibers which in use form a stationary phase comprising a plurality of pores through which a mobile phase can permeate and use of the same.

22 Claims, 9 Drawing Sheets

(51) Int. Cl.
| | |
|---|---|
| *B01J 20/28* | (2006.01) |
| *B01J 20/285* | (2006.01) |
| *B01J 20/30* | (2006.01) |
| *C07K 1/18* | (2006.01) |
| *C07K 1/22* | (2006.01) |
| *B01D 15/18* | (2006.01) |
| *B01D 15/38* | (2006.01) |
| *B01J 20/24* | (2006.01) |
| *B82Y 30/00* | (2011.01) |

(52) U.S. Cl.
CPC .......... *B01D 15/3804* (2013.01); *B01J 20/24* (2013.01); *B01J 20/285* (2013.01); *B01J 20/28007* (2013.01); *B01J 20/28038* (2013.01); *B01J 20/28083* (2013.01); *B01J 20/28085* (2013.01); *B01J 20/3007* (2013.01); *B82Y 30/00* (2013.01); *C07K 1/18* (2013.01); *C07K 1/22* (2013.01)

(56) References Cited

U.S. PATENT DOCUMENTS

| | | | |
|---|---|---|---|
| 6,923,908 B1 | 8/2005 | Thompson et al. | |
| 7,723,084 B2 | 5/2010 | Wang et al. | |
| 9,802,979 B2* | 10/2017 | Bracewell | B01D 15/361 |
| 2006/0093820 A1* | 5/2006 | Margarit-Puri | B29C 59/14 428/365 |

FOREIGN PATENT DOCUMENTS

| | | |
|---|---|---|
| WO | 03106655 A2 | 12/2003 |
| WO | 2010030900 A1 | 3/2010 |
| WO | WO 2013/068741 | 5/2013 |

OTHER PUBLICATIONS

Ma et al, "Electrospun polyethersulfone affinity membrane: Membrane preparation and performance evaluation", J. Chromatograph. B, No. 877, 2009, pp. 3686-3694.*
Ma et al, "Electrospun cellulose nanofiber as affinity membrane", Journal of Membrane Science, No. 265, 2005, pp. 115-123.*
Guest, "Evaluation of simulated moving bed chromatography for pharmaceutical process development", J. Chromatogr. A, No. 760, 1997, pp. 159-162.*
"HiTrap Blue HP" GE Healthcare Life Sciences, accessed from the internet on Oct. 31, 2017.
Charcosset, "Membrane Systems and Technology," *Comprehensive Biotechnology, 2nd Edition*, Ed. Murray Moo-Young, pp. 603-618, (2011).
Communication under Rule 71(3) issued in European Patent Application No. 14786703.0, dated Sep. 14, 2016.
Coskun, "Separation techniques: Chromatography," *North Clin Istanbul*, 3(2):156-160, (2016).
Dods et al., "Characterization of Electrospun Cellulose Acetate Nanofiber Adsorbers for Bioseparation" presented at 245th ACS National Meeting & Exposition, Apr. 9, 2013.
Dods et al., "Derivitization of electrospun cellulose nanofiber adsorbers for bioseparation," 245th American Chemical Society National Meetings & Exposition, Chemistry of Energy and Food, Apr. 9, 2013.
European Search Report issued in European Patent application No. 17154671.6, dated Jun. 2, 2017.
International Preliminary Report on Patentability issued in International Patent Application No. PCT/GB2013/052626, dated Apr. 12, 2016.
International Preliminary Report on Patentability issued in International Patent Application No. PCT/GB2014/000401, dated Apr. 12, 2016.
International Preliminary Report on Patentability issued in International Paten Application No. PCT/GB2012/052768, dated May 12, 2014.
International Search Report and Written Opinion issued in International Patent Application No. PCT/GB2013/052626, dated Aug. 21, 2014.
International Search Report and Written Opinion issued in International Patent Application No. PCT/GB2014/000401, dated Dec. 22, 2014.
International Search Report and Written Opinion issued in International Patent Application No. PCT/GB2012/052768, dated Feb. 2, 2013.
Invitation to Pay Additional Fees issued in International Patent Application No. PCT/GB2013/052626, dated May 8, 2014.
Lascu et al., "Ion-exchange properties of cibacron blue 3G-A sepharose (blue sepharose) and the interaction of proteins with cibacron blue 3g-a", *Journal of Chromatography A*, 283:199-210, (1984).
Notice of Allowance issued in U.S. Appl. No. 14/356,817, dated Jun. 27, 2017.
Office Action issued in European Patent Application No. 12784664.0, dated May 11, 2017.
Office Action issued in European Patent Application No. 12784664.0, dated Apr. 4, 2018.
Office Action issued in U.S. Appl. No. 14/356,817, dated Aug. 1, 2016.
Office Action issued in U.S. Appl. No. 14/356,817, dated Dec. 2, 2016.
Record of Telephone Consultation issued in European Patent Application No. 14786703.0, dated Sep. 6, 2016.
Search Report issued in Great Britain Patent Application No. GB1119192.1, dated Mar. 1, 2012.
Subramanian et al., "Dye-Ligand Affinity Chromatography: The Interaction of Cibacron Blue F3GA® with Proteins and Enzyme," *Critical Reviews in Biochemistry*, 16(2):169-205, (1984).
Turner, "A Simple and Colourful Procedure to Demonstrate the Principles of affinity Chromatography," *Biomedical Education*, 7(3):60-62, (1979).
Written Opinion issued in Singaporean Patent Application No. 11201602195Y, dated Dec. 21, 2016.
Zotero Report, Search Engine Results accessed from the internet on Oct. 10, 2013.
Aumann et al, "A Continuous Multicolumn Countercurrent Solvent Gradient Purification (MCSGP) Process", Biotechnology and Bioengineering, vol. 98, No. 5, 2007, pp. 1043-1055.
Bilad et al, Assessment and Optimization of Electrospun Nanofiber-Membranes in a Membrane Bioreactor (MBR), Journal of Membrane Science, No. 380, 2011, pp. 181-191.
Charcosset et al, "Purification of proteins by membrane chromatography", J. Chem. Technol. Biotechnol., No. 71, 1998, p. 95-110.
Charcosset, "Membrane Processes in Biotechnology: An Overview", Biotechnology Advances, No. 24, 2006, pp. 482-492.
Charcosset et al, "Membrane Chromatography", Membrane Processes in Biotechnology and Pharmaceutics, Jan. 2012, ISBN 978 0-444-56334-7, pp. 169-212.
Clark et al, "Technique for Ultrathin Layer Chromatography Using an Eltrospun, Nanofibrous Stationary Phase", Analytical Chemistry, vol. 81, 2009, pp. 4121-4129.
Cossins, et al, "Recombinant production of a VL single domain antibody in *Escherichia coli* and analysis of its interaction with peptostreptococcal protein L", Protein Expression and Purification, No. 51, 2007, pp. 253-259.
Farid, "Establishing Bioprocesses for Producing Antibodies as a Basis for Future Planning", Adv. Biochemical Engineering, Biotechnology, No. 101, 2006, pp. 1-42.
Ghosh, "Protein separation using membrane chromatography: opportunities and challenges", J. Chromatogr. A, No. 952, 2002, pp. 13-27.
Gottschalk et al, "Bioseparation in Antibody Manufacturing: The Good, the Bad and the Ugly", Biotechnology Progress, No. 24, 2008, pp. 496-503.
Hahn et al, "Mass transfer properties of monoliths", Sep. Sci. Technol., 37(7), 2002, pp. 1545-1565.

(56) References Cited

OTHER PUBLICATIONS

Hardick et al, "Nanofibre fabrication in a temperature and humidity controlled environment for improved fibre consistency", Journal of Materials Science, vol. 46, No. 11, Feb. 2, 2011, pp. 3890-3898.
Hardick et al, Nanofiber Adsorbents for High Productivity Downstream Processing, Biotechnology and Bioengineering, vol. 110, No. 4, 2013, pp. 1119-1128.
Jungbauer et al, "Chromatographic Media for Bioseparation", J. Chromatogr. A, No. 1065, 2005, pp. 3-12.
Kalbfuss et al, "Direct capture of influenza A virus from cell culture supernatant with Sartobind anion-exchange membrane adsorbers", J. Membr. Sci., No. 299, 2007, pp. 251-260.
Kaur et al, "Plasma-induced graft copolymerization of poly(methacrylic acid) on electrospun poly(vinylidene fluoride) nanofiber membrane", Langmuir 23(26), 2007, p. 13085-13092.
Levison, "Large scale ion-exchange column chromatography of proteins: comparison of different formats", J. Chromatogr. B, No. 790, 2003, pp. 17-33.
Ma et al, "Electrospun regenerated Cellulose nanofiber affinity membrane functionalized with protein A/G for IgG purification", Journal of Membrane Science, No. 319, 2008, pp. 23-28.
Matsumoto et al, "Preparation of ion-exchange fiber fabrics by electrospray deposition", Journal of Colloid and Interface Sciences, No. 293, 2006, pp. 143-150.
Menkhaus et al, "Electrospun nanofiber membranes surface functionalized with 3-dimensional nanolayers as an innovative adsorption medium with ultra-high capacity and throughput", Chem. Commun., No. 46, 2010, pp. 3720-3722.
Nakagaito et al, "Production of microfibrillated cellulose (MFC)-reinforced polylactic acid (PLA) nanocomposites from sheets obtained by a papermaking-like process", Composites Science and Technology, vol. 69, 2009, pp. 1293-1297.
Nicoud et al, "Simulated moving bed chromatography for preparative separations", LC-GC, vol. 18, No. 7, 2000, pp. 680-687.
Niven et al, "A method for the continuous purification of proteins by affinity adsorption", J. Biotechnol., No. 31, 1993, pp. 179-190.
Phillips et al, "Performance of a membrane adsorber for trace impurity removal in biotechnology manufacturing", J. Chromatogr. A, No. 1078, 2005, pp. 74-82.
Rathore et al, "Recent Developments in Membrane-Based Separations in Biotechnology Processes: Review", Preparative Biochemistry & Biotechnology, No. 41, 2011, pp. 398-421.
Roque et al, "An artificial protein L for the purification of immunoglobulins and Fab fragments by affinity chromatography", Journal of Chromatography A, No. 1064, 2005, pp. 157-167.
Ruthven et al, "Review Article No. 31, Counter-Current and Simulated Counter-Current Adsorption Separation Process", Chem. Eng. Sci., vol. 44, No. 5, 1989, pp. 1011-1038.
Sarfert et al, "Mass transfer limitations in protein separations using ion-exchange membranes", J. Chromatogr. A, No. 764, 1997, pp. 3-20.
Schulte et al, "Preparative enantioseparation by simulated moving bed chromatography", J. Chromatogr. A, No. 906, 2001, pp. 399-416.
Shi et al, "Mathematical analysis of affinity membrane chromatography", J. Chromatogr. A, No. 1081, 2005, pp. 156-162.
Ströhlein et al, "Continuous Processing: The Multicolumn Countercurrent Solvent Gradient Purification Process: A continuous chromatographic process for monoclonal antibodies without using Protein A", biopharm international, Feb. 2, 2007, 5 pages, Available at: <http://biopharminternational.findpharma.com/biopharm/article/articleDetail.jsp?id=401628&sk=&date=&pageID=3>.
Subramanian (Ed.), "Continuous Chromatography in Downstream Processing of Products of Biotechnology and Natural Origin", Bioseparation and Bioprocessing, vol. 1: Germany: Wiley-VCH, 2007, pp. 225-255.
Tejeda et al, "Optimal design of affinity membrane chromatographic columns", J. Chromatogr. A, No. 830, 1999, pp. 293-300.
Tennikov et al, "Effect of porous structure of macroporous polymer supports on resolution in high-performance membrane chromatography of proteins", J. Chromatogr. A, No. 798, 1998, pp. 55-64.
Weissenborn et al, "A study of combined filtration and adsorption on nylon-based dye-affinity membranes: separation of recombinant L-alanine dehydrogenase from crude fermentation broth", Biotechnol. Appl. Biochem., No. 25, 1997, pp. 159-168.
Wilcheck et al, "Thirty years of affinity chromatography", Reactive and Functional Polymers, No. 41, 1999, pp. 263-268.
Zheng et al, "Control of Pore Sizes in Macroporous Chitosan and Chitin Membranes", Ind. Eng. Chem. Res., No. 35, 1996, pp. 4169-4175.
Zhou et al, "Basic Concepts in Q Membrane Chromatography for Large-Scale Antibody Production", Biotechnol. Prog., No. 22, 2006, pp. 341-349.
Ziabari, et al, "Evaluation of electrospun nanofiber pore structure parameters", Korean J. Chem. Eng., No. 25(4), 2008, p. 923-932.

* cited by examiner

CHROMATOGRAPHY MEDIUM

CROSS REFERENCE TO RELATED APPLICATIONS

This application is a continuation of U.S. patent application Ser. No. 14/356,817 filed May 7, 2014, which is a national phase application under 35 U.S.C. § 371 that claims priority to International Application No. PCT/GB2012/052768 filed Nov. 7, 2012, which claims priority to Great Britain Patent Application No. 1119192.1, filed Nov. 7, 2011, all of which are incorporated by reference herein in their entirety.

FIELD OF INVENTION

The invention relates to chromatography medium, in particular to a chromatography medium comprising one or more electrospun polymer nanofibres which in use form a stationary phase comprising a plurality of pores through which a mobile phase can permeate.

BACKGROUND TO THE INVENTION

The biotechnology market is the fastest growing sector within the world pharmaceutical market accounting for 18% ($130 bn) of all market sales in 2010. This growth from 10% of the market share in 2002 is set to grow 48% between 2010-2016 from $130 bn to $192 bn [1]. Biopharmaceutical therapeutics encompasses four main biomolecule types: recombinant proteins, monoclonal antibodies (MAbs), viral vaccines, and plasmid DNA [2]. There are currently over 200 MAb products on the market with over 1000 in clinical trials [3]. As with most therapies there is a global pressure to continue developing new biotherapuetics while driving down the cost of production increasing their availability to a wider scope of the population [4,5]. This is particularly apparent to the downstream bioprocess (DSP) involved with the purification of biomolecules where chromatography alone accounts for over 50% of the cost of goods (COGs). Advancements in upstream processes over the last 15 years have seen fermentation titres grow from 0.5 g/L-50 g/L, and with this not being mimicked in the DSP there has been a clear drive in industry and academia for development [6,7].

Conventional chromatography involves various techniques for the separation of mixtures by passing a mobile phase through a stationary phase. The analyte (load/feed) is the mobile phase which is passed through the solid stationary phase in the form of a packed bed system based on adsorbent beads 50-100 µm in diameter. This stationary phase has differing affinities for different species contained in the load. The species that are either wanted (product capture) or not wanted (contaminant capture) bind to the stationary phase allowing for the purification of the product stream.

Affinity chromatography, developed by Pedro Cuatrecasas and Meir Wilchek [8], separates on the basis of a reversible interaction between a biomolecule and a specific ligand coupled to a chromatography matrix. The ligand most commonly used is Protein A due to its high selectivity which means equipment only needs to be scaled for product output requirements [9].

Other ligands in use include Protein G, Protein A/G and Protein L. Each has a different binding site recognizing different portions of antibodies which becomes useful when the product are antibody fragments as opposed to a whole MAbs [10,11].

Ion exchange chromatography is a widely used technique for the separation and purification of proteins, polypeptides, nucleic acids, due to its widespread applicability, high resolving power, high capacity and simplicity. Separation in ion exchange is obtained as biomolecules have ionisable chemical moieties which render them susceptible to charge enhancement as a function of ionic strength and pH. This implies biomolecules have differing degrees of interaction with an ion exchanger (insoluble matrix to which charged groups have been covalently bound) due to differences in their charges, charge densities and distribution of charge on their surface.

At a pH value below its PI (isoelectric point) a protein (+ve surface charge) will adsorb to a cation exchanger (−ve). At a pH above its PI a protein (−ve surface charge) will adsorb to an anion exchanger (+ve).

Consequently under a set of defined mobile phase conditions a biopolymer mixture may be chromatographed using an ion-exchange medium in suitable contactor. Dependent on the relative ionic charge of the components, some biopolymers will adsorb (adsorbates) and others will remain in solution. Desorption of bound material can then be effected resulting in a degree of purification of the target biomolecule [12].

The projected increase in the number of antibody therapies over the next 4 years along with improvements in upstream productivity, and process economics gives a requirement for improved downstream processing techniques. The limitations of chromatography systems are already being seen in the form of expensive resins and throughput volumes which gives strong argument to the demand for improving technologies in this field.

There are two major drawbacks of traditional packed bed column chromatography; pressure drop and residence times. The operational flow rates in a packed column are limited by the pressure drop across the column. The compressible packed bed is susceptible to high pressures which can have drastic consequences with implosion of the column itself. At such a stage in the bioprocess where material is extremely high value this can have severe economic impacts for any company. Packed bed columns usually employ porous ca. 50 µm diameter Agarose beads as highly porous structures that achieve a suitable surface area for adsorption. However the system relies on diffusion for the large target biomolecules to come into contact with these surfaces which requires long residence times. As such the flow rates must be kept at a relatively low value, often in the range of 100 cm/h, which therefore limits the throughput of the system. The concern here is regarding the inefficient use of expensive chromatography resins [13,14].

Membrane adsorbers have been commercially available for many years now, but these have only proven to be useful at small scale [15]. Using membrane chromatography allows for operation in convective mode thereby significantly reducing the diffusion and pressure drop limitations seen in column chromatography. Operating at much higher flow rates offers advantages such as decreasing process time thereby increasing throughput and reducing damage to product biomolecules due to shorter exposure to unfavourable medium [16].

Kalbfuss, et al. described how the use of a commercially available anion exchange membrane proved to be a potentially viable option for the removal of viral particles operating in contaminant capture mode with relatively high flow rates of 264 cm/h performing consistently well [21].

Zhou and Tressel carried out a cost analysis based on their experimentation using anion (Q) exchange membranes to remove four model viruses. Results suggested that the economic viability of the Q membrane over the Q column was highly dependent of production scale along and specific to each production process [22]. Research suggests that there is potential for Q membranes though the advantages do not seem significant enough for the industry to adopt such a significant change. Additionally, chromatographic operations that run in capture mode such as cation-exchange chromatography (CEX) and affinity chromatography have proven to be much more challenging with poor peak resolution observed [23]. One aspect working in the favour of membrane chromatography systems is the increased uptake of disposable systems in industry, of which membranes hold many advantages over conventional packed bed columns.

There are many examples of membrane adsorbers in use and in continuing development [24-29].

It is clear from the work that is already published on membrane adsorbers that several important properties are required relating specifically to the membrane structure. For efficient utilisation of binding surface area the inlet flow must have even dispersion and the pore size distribution must be small so as to minimize any channelling. Membranes used in the chromatography method discussed above also excel when combined with other technologies.

Simulated Moving Bed (SMB) technology has been in use for many years in the chemical industry, originally developed for difficult petrochemical separations [32]. Later its use in the pharmaceutical industry quickly grew due to its strong ability to perform chiral separations with the first US Food and Drug Administration's (FDA) approved drug manufactured by SMB technology reaching the market in 2002 with Lexapro [33]. Traditionally the powers of SMB to carry out separation based on the different moieties of complex components have been focused on systems that yielded poor productivity using column chromatography. Today however more focus is being placed on bind/elute chromatographic processes in an effort to improve the utilisation of expensive adsorptive resins and reduce the large volumes of buffers used at large scale production [34,35].

In this fashion SMB chromatography operates by employing three or more fixed adsorbent substrates, such as packed bed columns, with buffer and feed streams flowing into to system continuously. A counter-current solid substrate is simulated by switching various valve inlet ports periodically.

SUMMARY OF THE INVENTION

A first embodiment of the invention relates to a chromatography medium comprising one or more electrospun polymer nanofibres which in use form a stationary phase comprising a plurality of pores through which a mobile phase can permeate. The invention may also be a chromatography medium having a plurality of pores comprising one or more polymer nanofibres. Typically, the stationary phase is a membrane of nanofibres, which may have a thickness of 10 nm to 15 mm, often 10 µm-10 mm, or 100 µm-1 mm. Ensuring that the membranes do not exceed these parameters is desirable as, if a membrane is too thin, the membrane may rupture under high flow rates and if a membrane is too thick, blockages may occur which could lead to damaging build ups of pressure and/or decreased performance.

The polymer nanofibres may be non-woven nanofibres. Using a randomly deposited fibre mat (non-woven) structure can encourage impeded flow thereby discouraging channelling [30].

The polymer nanofibres are electrospun. Electrospinning provides nanofibres with consistent dimensions and can easily be tuned (for example, by varying atmospheric properties while spinning) to make nanofibres of different proportions. Electrospinning is a technique that also demonstrates excellent distribution properties, especially useful when creating layered membranes [31]. Nanofiber mass transfer characteristics have been shown to be similar to those in a monolith structure which allow for flow rate independent separations [43].

The polymer used in the present invention is not limited to any specific polymer and can be tailored for specific use. The polymer may be for example: nylon, poly(acrylic acid), polyacrylonitrile, polystyrene, polysulphone, polyacrylonitrile, polycaprolactone, collagen, chitosan, agarose and polyethylene oxide and combinations thereof. The polymer may be derivatised to enhance the solubility and/or other properties of the polymer in order to improve its suitability to be electrospun. The derivatised polymer (for instance polyether sulfone, cellulose acetate or poly(acrylonitrile-co-acrylic acid) can be treated post electrospinning to regenerate the original polymer or derivatise further to create a new functionality. The polymer used in the invention is typically cellulose. Cellulose is often used as it is readily available, cheap, biodegradable, biologically compatible and has a hydrophilic surface resulting in low non-specific binding.

The polymer nanofibres may be covalently cross-linked. Once an electrospun network of nanofibres has been made, the nanofibres may be fused together at points were nanofibres intersect one another by thermal, chemical or other methods. This leads to improved manual manipulation characteristics.

The nanofibres may have a diameter of 10 nm to 1000 nm. The nanofibres may have a diameter of 200 nm to 800 nm and may even have a diameter of 300 nm to 400 nm. Nanofibres of this size yield improved consistency of pore size and size distribution.

The nanofibres may have a mean length of greater then 10 cm. Nanofibres generated by electrospinning are typically much longer than the nanofibres found in conventional chromatography media. Longer nanofibres deliver improved layering properties. In some cases, where the electrospinning comprises a fibre emanating from a single source, a single continuous fibre may be produced and the membrane formed from this fibre alone, or from a small number (1, 2, 3, 4, 5, 6, 7, 8, 9, 10) of long fibres.

The pores of the stationary phase may be 10 nm to 10 µm in diameter, often 25 nm to 5 µm and can be 50 nm to 2 µm in diameter. Use of pore sizes within these size ranges can help to minimise fouling of the chromatography medium and decrease product loss due to polarization, concentration and rejection at particle interfaces [18]. However, the pores remain small enough to minimise the loss of target components passing through the membrane without coming into contact with the medium. The selection of these pore sizes ensures good utilisation of capacity [19] and sharper breakthrough curves [20]. Kaur et al. [39] demonstrated that for a membrane structures with similar pore size the nanofibre structures were 1.5-2 times more permeable to aqueous flow than a traditional membranes produced by phase inversion. This is due to the relatively high surface porosity that the electrospinning process yields. Ziabari et al. [40] showed that a non-woven nanofibre membrane with average fibre diameter of 300 nm contained an average pore size of ca. 500 nm, yet yielding a porosity of 49%. By electrospinning nanofibre membranes we are able to achieve a high level of surface porosity of high distribution well above what could be expected from traditionally formed membranes as in their case the relationship of decreasing surface porosity with decreasing pore size is dominant [41].

The pores may have a narrow size distribution, wherein the standard deviation in pore diameter is preferably less than or equal to 250 nm. Pore size uniformity is one of several factors as well as, axial and radial diffusion and sorption kinetics, that has been shown to have an impact on key performance factors in chromatography (particularly affinity chromatography) such as breakthrough curve (BTC) sharpness [17].

A second embodiment of the invention relates to the use of the media in chromatography. The medium is typically for use in ion exchange chromatography and may also be for use in affinity capture chromatography. Ion exchange and affinity capture chromatography are particularly suitable for use with the chromatography medium of the invention as the medium can be readily functionalised to interact with target molecules. This gives the medium high capacity whilst allowing large volumes to be processed. Multi-point attachment of ligands and the like to the medium is possible and gives minimal leakage and results in low product contamination.

The invention may also be for use in isolating biological molecules from the mobile phase. Typically, these biological molecules have a molecular weight of 1 kDa to 200 kDa and may have a molecular weight of 10 kDa to 100 kDa. Often monoclonal antibodies are of molecular weight around 150 kDa, often in the range 100-200 kDa. The invention may be used to isolate biological molecules selected from: recombinant proteins, monoclonal antibodies, viral vaccines and plasmid DNA.

The invention may also be for use in enzyme catalysed reactions. Typically enzymes are immobilised on the nanofibres. The enzymes may be immobilised by adsorption, entrapment or cross-linkage.

The invention also typically employs a simulated moving bed (SMB) system. The SMB system can be employed so as to exploit the fast mass transfer properties of the nanofibre adsorbents. This leads to a greater utilisation of the medium performing the desired separation of the feed stream yielding a continuous product stream by switching outlet ports [36-38]. Further, SMB chromatography lends itself well for industrial, continuous purification as does the medium of the invention which may be a membrane. Membranes are easier to replace than conventional chromatography media (e.g. silica powder) and therefore leads to reduced disruption of continuous purification processes.

In embodiments of the invention employing an SMB system flow distribution may be optimised for maximum utilisation of the adsorbent. Preferably the fluid is in plug flow. Plug flow allows mass transfer across the entire binding surface of the adsorbent and can provide improved separation, as measured for example by BTC sharpness.

A third embodiment of the invention relates to a cartridge for use in chromatography comprising: two or more membranes including the medium of the invention arranged in series; and a holding member to fix the membranes in place relative to one another. Including multiple membranes further improves the cartridge's filtration performance. Providing the medium in the form of a cartridge also allows the medium be easily inserted and removed from industrial purification systems. The holding members support the nanofibre membrane and aid flow distribution.

In some examples the membranes may be interspersed with frits. As used herein the term "frit" is intended to be given it's common meaning in the art, and refers, for instance, to a rigid porous structure. The fits may offer support and promote dispersion in an effort to create plug flow to maximise utilisation of the adsorbent surface. The ratio of membranes to frits may be in the range 5:1-1:5. Interspersion may be regular, wherein a regular pattern of membrane to frit is provided, such as membrane-membrane-frit in a 2:1 membrane:frit system, or irregular, wherein the ratio of membrane:frit is as defined, but the ordering of the layers does not form a pattern. In many cases, there will be more membranes than frits, and so the ratio of membranes: frits would be in the range 5:1-1:1. Often the ratio of membranes:frits will be 1:1, and the interspersion will be a regular membrane-frit-membrane-frit pattern.

DESCRIPTION

The invention will now described by reference to the following figures.

Figure 4B:
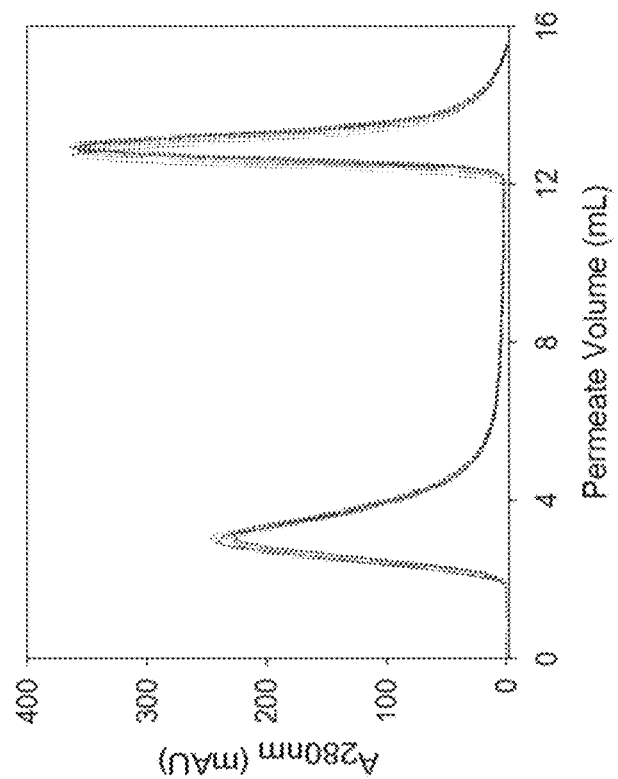
Figure 4A:
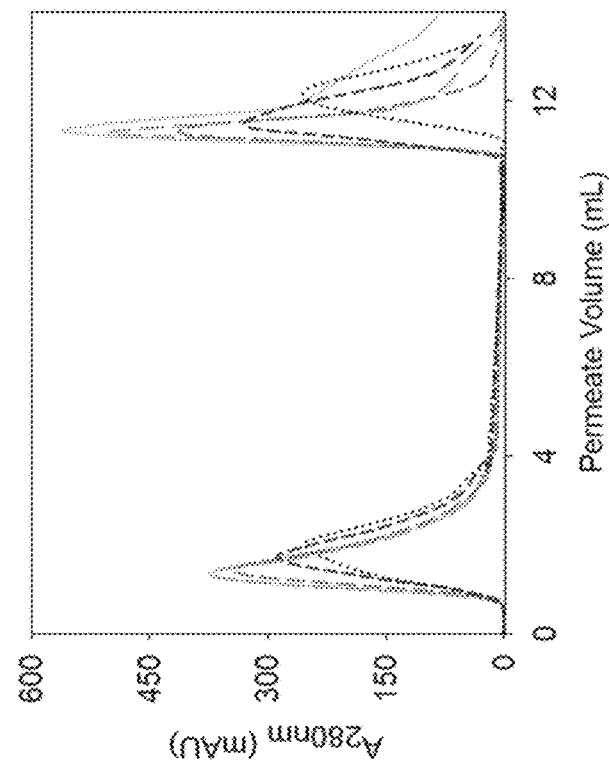

FIG. 4*a* shows binding/elute profiles of a nanofibre cartridge of the invention at varying flow rates in which, starting from light grey full line to dark grey dotted line: 72 cm/h (2,400 CV/h), 96 cm/h (3,200 CV/h), 120 cm/h (4,000 CV/h), 240 cm/h (8,000 CV/h) and 360 cm/h (12,000 CV/h). FIG. 4*b* shows a chromatogram showing 10 repeat bind/elute profiles of a nanofibre cartridge of the invention at a fixed loading flow rate of 240 cm/h (8,000 CV/h).

Figure 5:
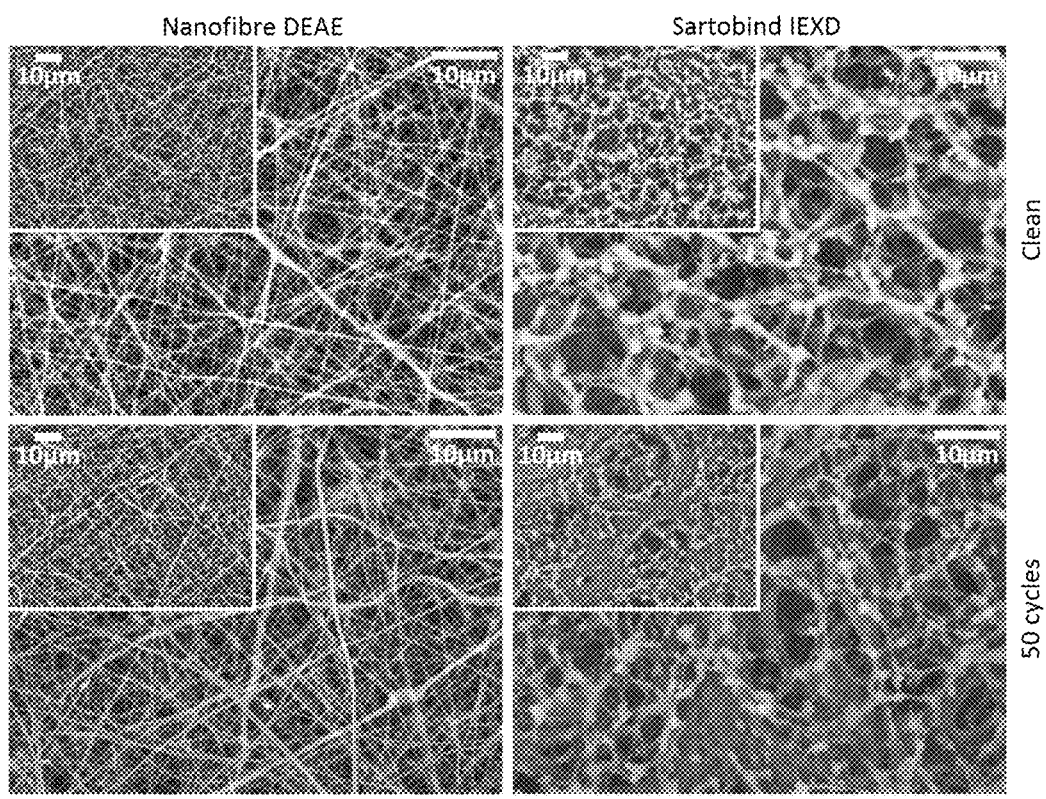

FIG. 5 shows SEM images of a nanofibre cartridge of the invention and Sartobind IEXD membrane before and after a feed stream of centrifuged and 0.45 µm filtered yeast homogenate. Top SEM images show clean membranes at two magnifications, while the bottom images show membranes after 50 cycles of clarified homogenate loading. The scale bar indicates 10 µm.

Figures 6A, 6B:
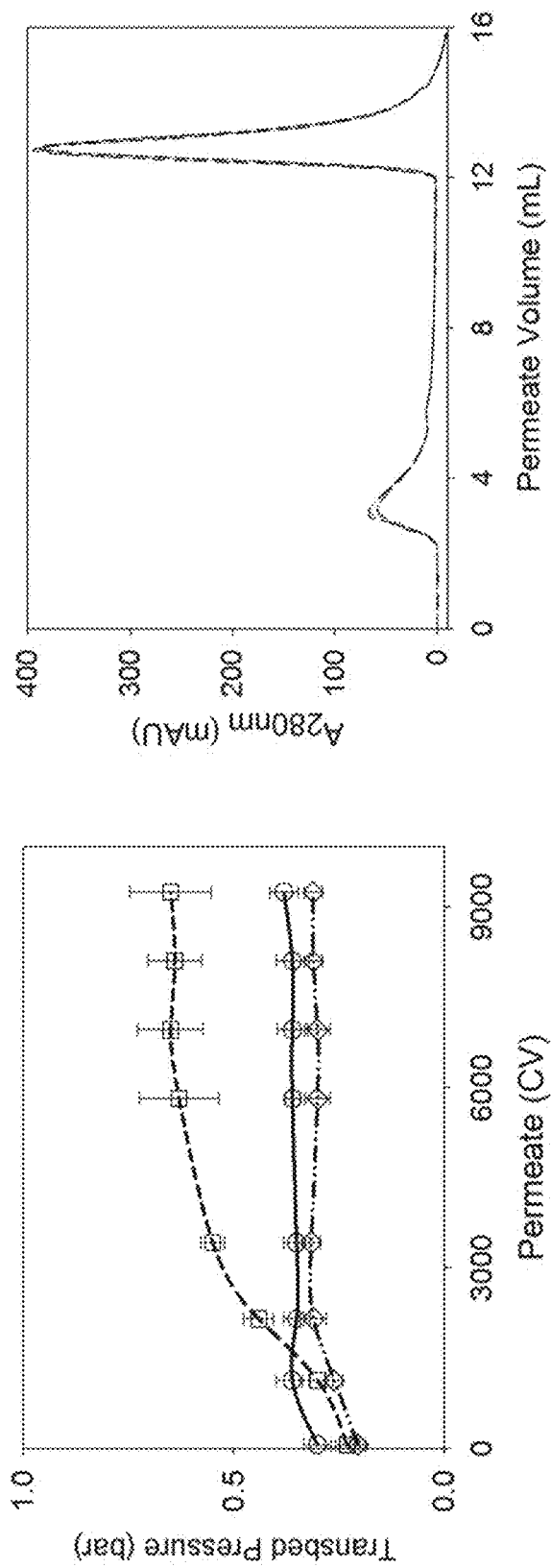

FIG. 6*a* shows the results of a filtered load investigation showing pressure flow relationships for equivalent volumes of: ○ Sartobind IEXD, □ Sartobind Epoxy-DEAE, and ◇ DEAE nanofibre of the invention. Error bars are ±1 standard deviation of the sample population. FIG. 6*b* shows two bind/elute profiles before and two after clarified homogenate loading and CIP of the DEAE nanofibre cartridge of the invention at a fixed loading flow rate of 240 cm/h to demonstrate reproducibility after clarified yeast homogenate loading (2 mL) and CIP (20 mL 1M NaOH).

Figure 7:
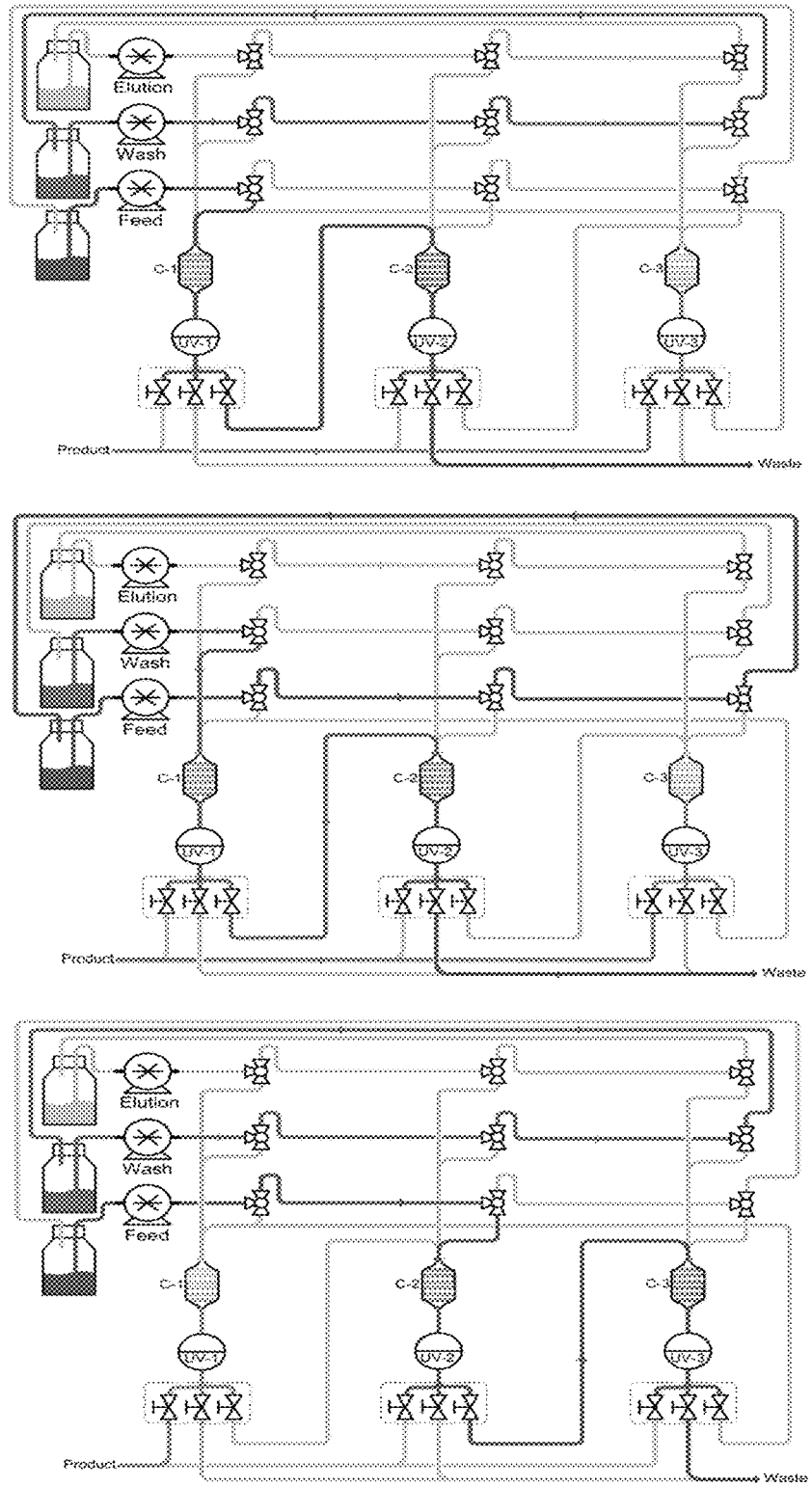

FIG. 7 shows a design drawing of a simulated moving bed (SMB) system showing different phases of operation.

Figure 8:
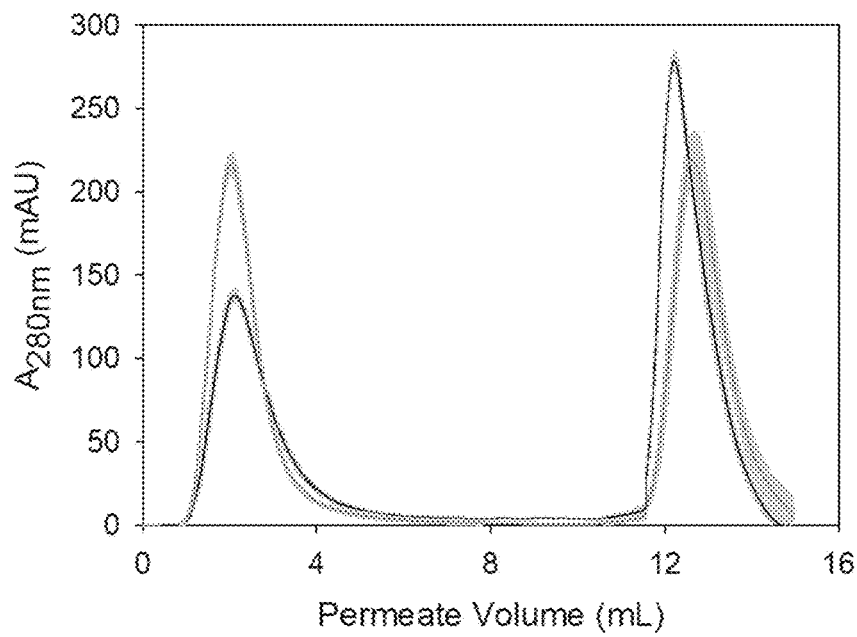

FIG. 8 shows the average separation results for DEAE nanofibre adsorbent of the invention (Black) and Sartobind IEXD (Dark Grey). ±1 standard deviation of the sample population is shown by the shaded grey area around each curve.

Figure 9:
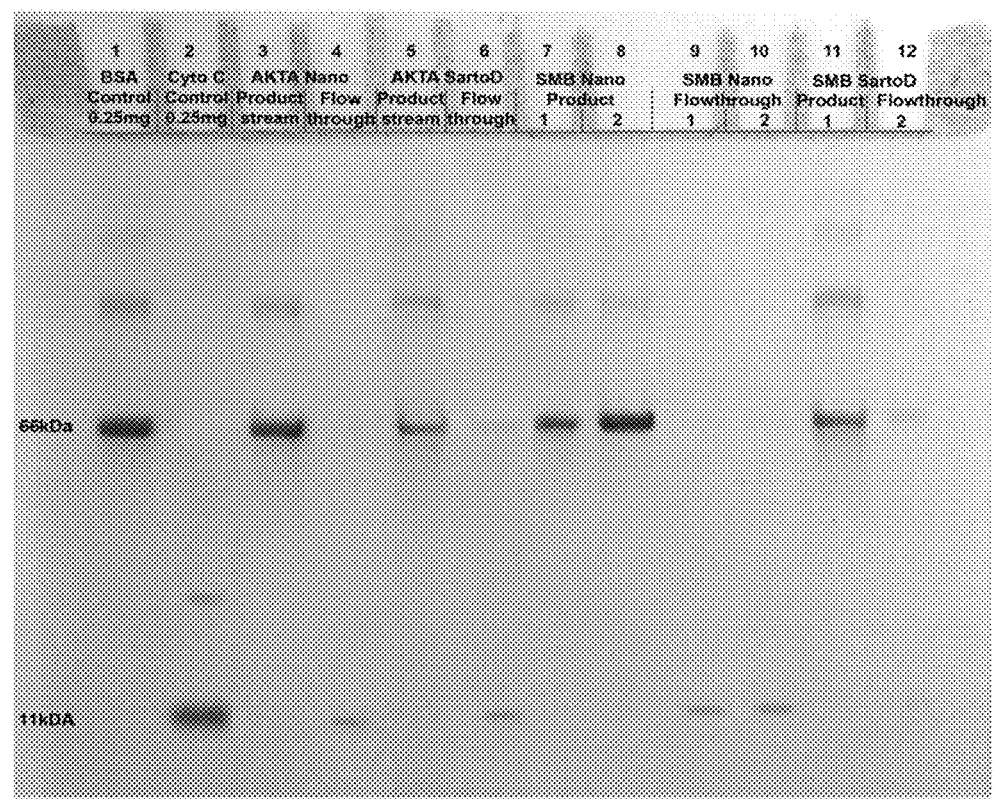

FIG. 9 shows an SDS Page Gel showing denatured components of 12 protein samples.

Figure 10:
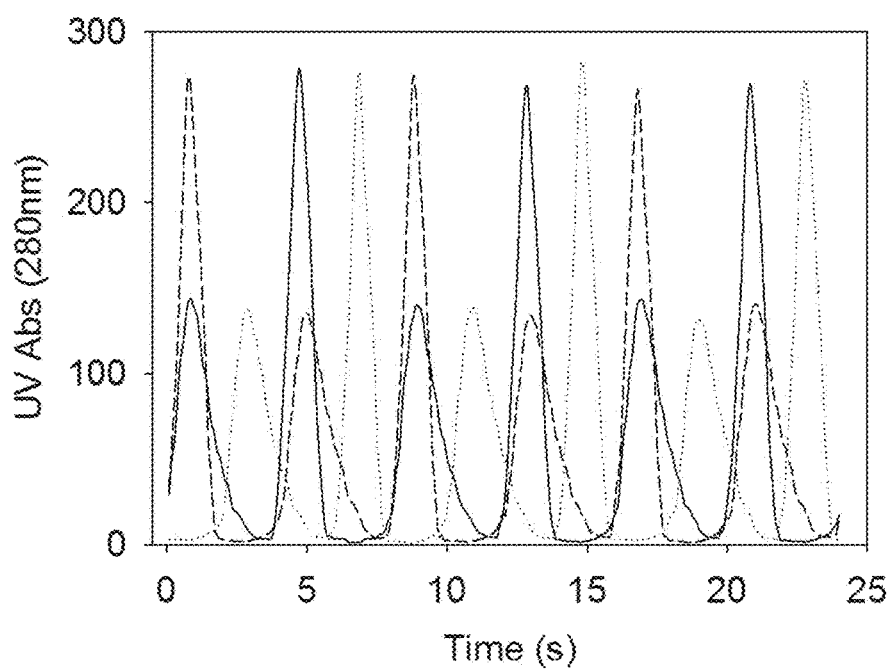

FIG. 10 shows chromatogram data from the SMB operation of 2-component separation; UV absorbance traces were a snapshot for a 25 second time period taken from the three different adsorbent columns during one SMB operation.

Figure 11:
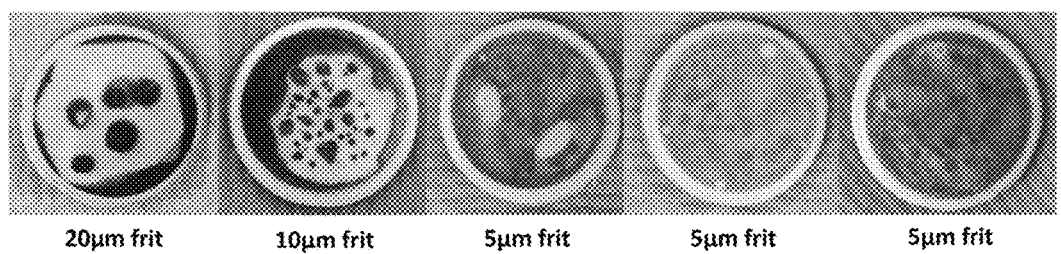

FIG. 11 shows photographs from a coomassie blue dye flow distribution study utilising different pore size frits.

Figure 1:
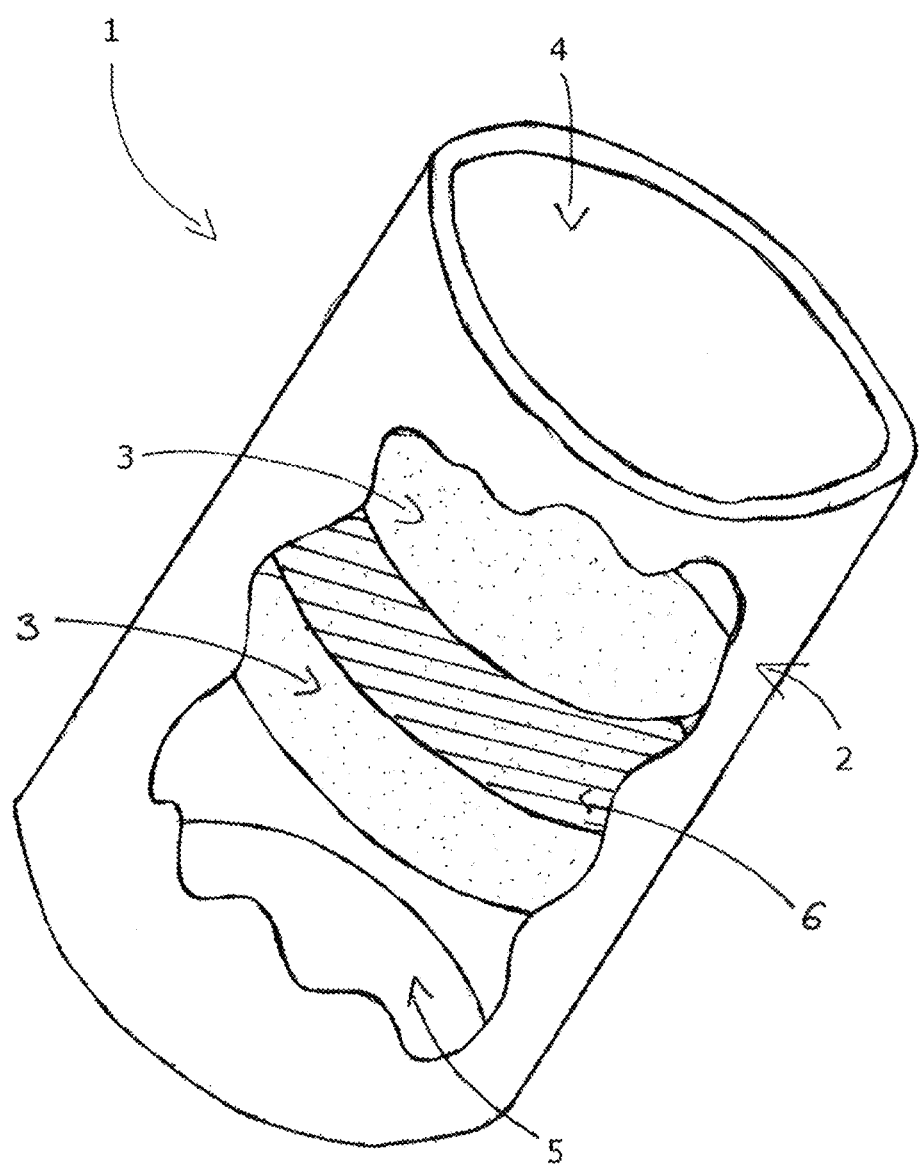
FIG. 1 shows a schematic image of the cartridge of the invention.

As shown in FIG. 1, cartridge (1) comprises a holding member (2) within which multiple membranes (3) are arranged in series. In this embodiment, one or more frits (6)

are also present, in a 1:1 ratio with the membranes of the invention. The cartridge also has an inflow port (4) through which a mobile phase can be passed and a corresponding outflow port (5).

Figure 2:
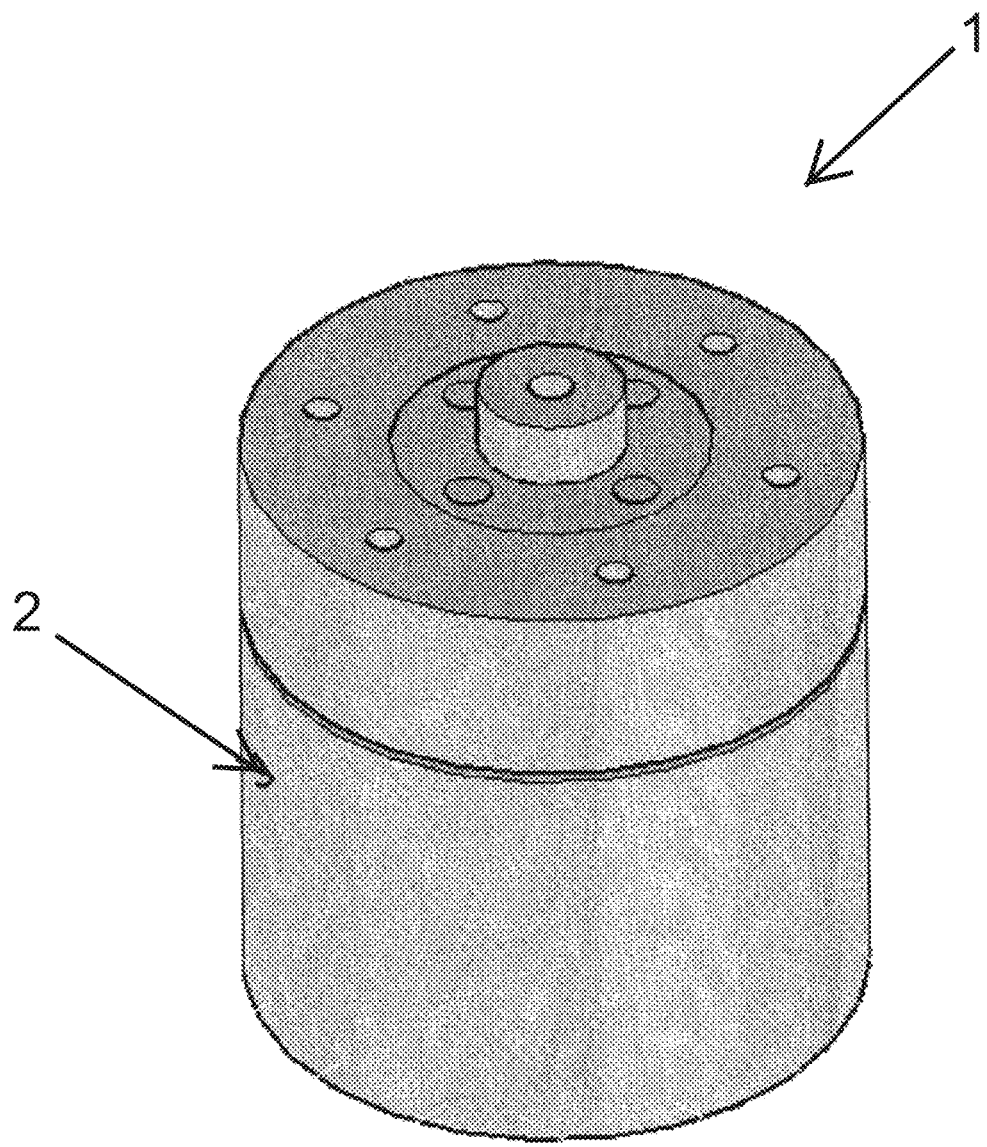
FIG. 2 shows an alternative embodiment of the cartridge of the invention.
Figure 3:
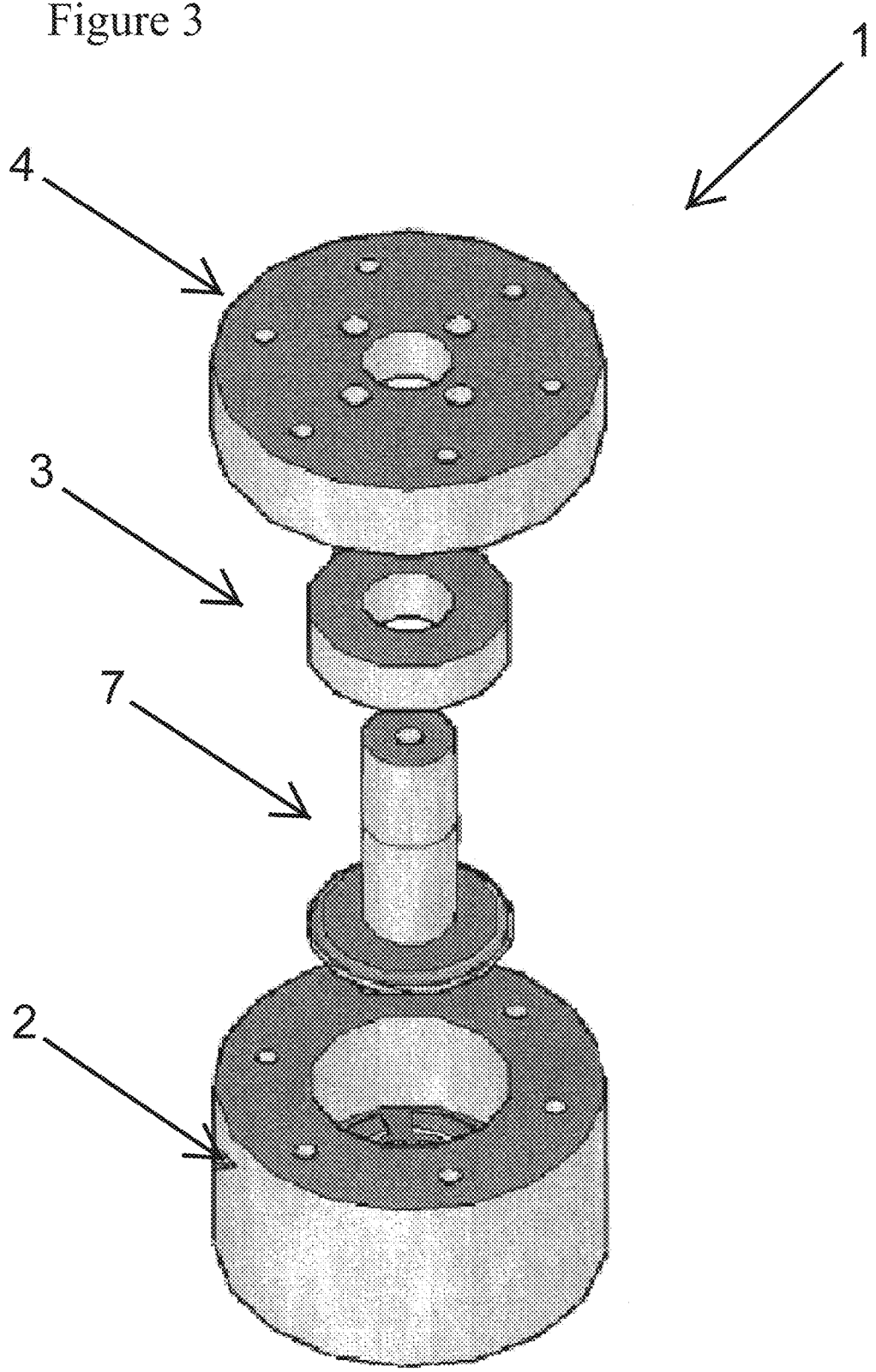
FIG. 3 shows an exploded image of the embodiment of FIG. 2.

FIGS. 2 and 3 show an alternative embodiment of the cartridge of the invention. In this embodiment holding member (2) comprises a support column (7) onto which the membranes (3) and, where present, frits (7), may be placed.

Unless otherwise stated each of the integers described in the invention may be used in combination with any other integer as would be understood by the person skilled in the art. Further, where numerical ranges are provided, it is intended that these represent a specific disclosure not only of the end points of the range, but of each value, in particular integers, within the range. In addition, although all aspects of the invention preferably "comprise" the features described in relation to that aspect, it is specifically envisaged that they may "consist" or "consist essentially" of those features outlined in the claims.

EXAMPLES

A solution of cellulose acetate (CA) (Mr=29,000; 40% acetyl groups; 0.20 g/mL) in acetone/dimethylformamide/ethanol (2:2:1) was electrospun to obtain CA nanofibre non-woven membranes.

Sartorious Stedim Sartobind membranes (Sartorius Stedim UK Ltd. Epsom, UK) were cut to size and used as a comparison.

Electrospinning

The process was carried out in a ClimateZone climate control cabinet (a1-safetech Luton, UK) which allows the process to be performed under controlled atmospheric conditions. The temperature and RH were selected and kept constant throughout the fabrication at 25° C. and 60% RH.

A 50 mL polymer solution was loaded into a sterile syringe and attach to a Harvard PHD 4400 syringe pump (Harvard Apparatus Ltd. Kent, UK), with a programmable flow rate range from 0.0001 up to 13.25 L/h, to deliver the polymer solution to a 0.5-mm ID stainless steel micro needle. The pump is set at a flowrate of 800 µL/h. The tip of the needle was placed 30 cm above the grounded collector. The collector used was an earthed aluminium rotating drum (15 cm diameter×25 cm width) covered with low surface friction polymer rotating at a speed of 100 rpm. The process was run for 60 h. These conditions were selected based on preliminary experiments and are known to yield solid dry nanofibres with diameters from 300-400 µm.

Post Electrospinning Modification

Once electrospun the nanofibres are removed from the collection drum and placed into a drying oven at 213° C. for ten minutes. This is below the glass transition temperature of cellulose acetate but it is hot enough to begin fusing joints where nanofibres intersect, thereby increasing the structural stability of the fibre matt giving improved manual manipulation characteristics.

After this process the fibre matt is cut into multiple 25 mm diameter discs using a wad punch. These discs are then ready for packing into a PALL Easy Pressure Syringe Filter Holder (Pall Life Sciences, Portsmouth, United Kingdom).

Once packed into a ~100 mg cartridge (~6 layers ~0.4 mm bed height) the membrane is treated with 200 mL 0.1M NaOH in a solvent mixture of 2:1 De-ionised (DI) $H_2O$: Ethanol for 24 hours fed continuously in a cyclical manner using a Watson Marlow 205U Peristaltic pump (Watson-Marlow Pumps Group Falmouth, UK) at a rate of 15 mL/min. After the saponification/deacetylation process to form a regenerated cellulose membrane 200 mL DI $H_2O$ is passed through the membrane at the same flowrate. Anion-exchange surface functionality is then obtained by recycling 20 mL warm (40° C.) 15% DEACH aqueous solution at 20 mL/min for 10 minutes. Cartridges are subsequently removed from the filter holder housing and left in 20 mL hot (80° C.) 0.5M NaOH on a hot plate stirrer with gentle agitation. Finally the membrane cartridges are rinsed in multiple volumes of DI $H_2O$ before being packed ready for use.

Permeability

The permeabilities of load and buffer solutions through packed nanofibre were compared with the permeabilities of a commercially available alternative membrane, Sartorious Sartobind membrane, using an AKTA Explorer (GE Healthcare Life Sciences, Buckinghamshire, UK) with online pressure measurement capabilities. The pressure drop of the system was first evaluated using the empty membrane holder evaluated at flow rates ranging from 1 mL/min-100 mL/min. The different membranes were then evaluated with the system pressure drop being subtracted to calculate the permeability of each membrane at the varying flow rates.

Equilibrium Binding

The previously prepared 25 mm diameter AEX membrane cartridges have a total film surface area of 4.91 $cm^2$, an approximate mass of 100 mg, and an approximate wet bed height of 0.3 mm suggesting a bed volume ~0.17 mL. Equilibrium binding studies were carried out to find the total capacity of the DEAE AEX membranes for of a model protein Bovine Serum Albumin (BSA). This was carried out in the sealed filter holder system using sterile disposable syringes (BD biosciences) and a Harvard PHD 4400 syringe pump (Harvard Apparatus Ltd. Kent, UK). The DEAE membrane was equilibrated with 10 mL wash buffer 10 mM Tris, pH 8.0 buffer a rate of 40 mL/min. 20 mL of 1 mg/mL BSA (in wash buffer) was then loaded onto the membrane at a rate of 40 mL/min. This load sample was then pulled back through the membrane at the same rate with this process being repeated continuously for 1 hour in order to expose the membrane to the model protein for a sufficient length of time to reach maximum binding capacity. Collection of the load stage was followed by five wash stages with 1 mL wash buffer before desorption of the model protein was carried out by three elution stages each with 1 mL 1M NaCl 10 mM Tris, pH 8.0 elution buffer at a rate of 40 mL/min.

All wash and elution stages followed the same dual flow pattern used with the loading for a period of two minutes each. At each stage in this process the eluate was collected and UV absorbance readings at 280 nm were taken using Jasco V-630 UV spectrophotometer (Jasco (UK), Essex, United Kingdom). Studies were repeated on three occasions in order to ensure replicates were reproducible. Mass balances were conducted to ensure the traceability of all model protein introduced into the system. The same protocol was run with Sartobind DEAE membranes and Sartobind epoxy membrane functionalised in house for comparison. Control samples were run under the same conditions to discount possible binding to the filter holder surface or non-specific binding of BSA to non-functionalised membrane, regenerated cellulose (RC) membrane.

Dynamic Breakthrough

A more useful determination of the binding capacity of these nanofibre adsorbents is their dynamic binding capacity employing operational flowrates observed as suitable in previous permeability studies. Experiments were completed using the AKTA Explorer (GE Healthcare Life Sciences, Buckinghamshire, UK) with online measurement of UV absorbance (280 nm), pH, and conductivity.

DEAE nanofibre membrane cartridges were prepared in the same way as before in order to determine the dynamic capacity of the membranes for of a model protein Bovine Serum Albumin (BSA). The DEAE membrane was equilibrated with 10 mL wash buffer 10 mM Tris, pH 8.0 buffer a rate of 6000 CV/h. 1 mg/mL load sample of BSA were then loaded onto the membrane until 100% breakthrough at various flow rates from 24,000 CV/h-4000 CV/h. 10 mL wash buffer was then passed through the saturated membrane before 5 mL 100% 1M NaCl 10 mM Tris, pH 8.0 elution buffer was introduced to the membrane at a range of flow rates from 8000 CV/h-2000 CV/h.

Online UV absorbance readings at 280 nm were taken throughout the experiment.

A simulated moving bed system was designed and built using a series of Burkert solenoid valves (Bürkert Fluid Control Systems, Stroud, UK) 1/16" Peek tubing, Peek connectors, and a Perimax 12 peristaltic pump (Spetec GmbH, Erding, Germany). UV sensors were placed on the exit of each of the three filter holders which was connected to a National Instruments analogue input module (National Instruments Corporation (U.K.) Ltd, Newbury, UK) to record the UV absorbance at 280 nm. Three National Instrument digital output modules were used to control the valve positions with NI Labview 2010 software used to sequence the control and compute the analogue input signals.

Chemical Surface Derivatisation (FT-IR)

ATR-FTIR spectrum of the CA, RC and modified RC membrane was obtained on a Thermo Scientific Nicolet iS10 FT-IR Spectrometer fitted with an attenuated total reflectance (ATR) module (Loughborough, UK) The Attenuated total reflectance technology allows for direct analysis of solid, liquid or gas samples without further preparation. Spectra were recorded in the range 4000-500 cm$^{-1}$ by an accumulation of 50 scans. A background was measured with 10 scans prior to each sampling. The manufacturer supplied software OMNIC was used to normalise and analyse the spectra.

Scanning Electron Microscopy (SEM)

A Hitachi TM-1000 Tabletop microscope (Hitachi High-Technologies Europe Gmbh) was used to monitor the physical properties of the nanofibres after electrospinning and during/post modification to ensure than the nanofibre form remained consistent. Samples were analysed from three SEM images each with 20 individual measurements of nanofibre diameters.

Protein Concentration (UV)

UV spectrophotometer Jasco V-630 (Jasco (UK), Essex, United Kingdom) was used to determine the concentration of BSA in solution. A full spectrum from 320 nm-240 nm was recorded with a scan speed of 200 nm/min and a step of 1 nm.

AKTA Explorer (GE Healthcare Life Sciences, Buckinghamshire, UK) was used to measure online absorbance at 280 nm, pressure, feed rates and conductivity throughout the experiments allowing for full run profiles to be analysed.

Reproducibility, Mass Transfer, and Life Cycle Performance

Reproducibility in performance was shown based upon 10 bind/elute runs of the DEAE nanofiber cartridge at a fixed loading flow rate of 240 cm/h. The absorbance flow profiles shown in FIG. 4b clearly show that the adsorbent operates in a reproducible manner during laboratory scale experiments using standard liquid chromatography apparatus.

Bind/elute profile of the DEAE nanofibre cartridge at varying flow rates was also investigated and is shown in FIG. 4a: starting from light grey full line to dark grey dotted line; 72 cm/h (2,400 CV/h), 96 cm/h (3,200 CV/h), 120 cm/h (4,000 CV/h), 240 cm/h (8,000 CV/h) and 360 cm/h (12,000 CV/h). The nanofibre adsorbents demonstrated high mass transfer characteristics that are desired for a high productivity separation with no observed peak broadening in the separation with increased flow rate when plotting the chromatogram against time indicating that mass transfer is a minimal component of the resistance in the column. The integrated areas of the elution peaks in the UV absorbance profiles remained constant demonstrating equivalent capture and elution over the range of flow rates tested. The adsorbents tested had a bed height of 0.3 mm and column volume of ~0.15 mL.

Fouling studies utilized clarified yeast homogenate to give an understanding of how the adsorbent would perform with complex load conditions. Initial adsorbent fouling studies conducted in a conventional process manner showed no change in trans-bed pressure over 50 cycles of loading, washing, eluting, cleaning-in-place (CIP), and equilibration. Scanning electron microscopy images showed no visible build-up of homogenate on the nanofibre adsorbents after 50 cycles. Conversely, the Sartobind IEXD membranes showed some fouling (FIG. 5) illustrating that with standard CIP conditions (1M NaOH) nanofibre adsorbents were more easily cleaned.

In the continuous homogenate loading experiments both the DEAE nanofibre cartridge and Sartobind IEXD membrane performed well with the clarified homogenate; running for over 9,000 column volumes with only a small increase in trans-bed pressure (FIG. 6a). The Sartobind Epoxy-DEAE derivatized membrane was affected more by this homogenate most likely due to the smaller pore sizes in this membrane. The chromatogram of BSA capture by nanofibre adsorbent before and after clarified homogenate loading and CIP shown in FIG. 6b demonstrates that the nanofibre cartridge performed reproducibly irrespective of the complex feed and harsh CIP conditions employed, confirming the observation shown in FIG. 5 that there was little build-up of homogenate on the nanofibre surface during these studies.

Simulated Moving Bed Operation

A simulated moving bed (SMB) system was designed and built using a series of Burkert solenoid valves (Burkert Fluid Control Systems, Stroud, UK), 1/16" Peek tubing, Peek connectors, and three Dionex P580 P HPLC pumps (Dionex Softron GmbH, Germany). UV sensors were placed on the exit of each of the three adsorbent holders which were connected to a National Instruments analogue input module (National Instruments Corporation (U.K.) Ltd, Newbury, UK) to record the UV absorbance at 280 nm. Three National Instrument digital output modules were used to control the valve positions with NI Labview 2010 software used to sequence the control and compute the analogue input signals. FIG. 7 shows the SMB design layout operating at 3 different phases of the process.

Use of Nanofibre Adsorbents in the SMB System

The mass transfer properties of these nanofibre adsorbents make them ideally suited to SMB operation where product can be rapidly loaded and removed in a multiple reuse fashion. FIG. 8 shows the flow through of cytochrome C+unbound BSA as the first peak during loading of 2-component mixture and the elution of BSA as the second peak. The graphs show the reproducibility over 12 equivalent runs for each adsorbent type. This shows that for the conditions chosen, the nanofibre adsorbents performed favourably for an equivalent volume of adsorbent. The nanofibre adsorbent captured and eluted 99% of the BSA loaded, whereas the Sartobind IEXD membrane only captured 70%. Over the 12 runs for each adsorbent the standard deviation was calculated to show that the nanofibre adsorbent operated more consistently, though both types demonstrated high levels of consistency. The results shown in FIG. 8 demonstrate that for the conditions chosen the nanofibre adsorbent captured and eluted more of the target molecule (BSA) from the 2-component mixture. The tighter shaded region also indicates a more consistent performance in separation. In each case the adsorbent tested had a bed height of 0.3 mm and column volume of ~0.15 mL Samples from the 2-component separation studies were separated by SDS Page for analysis and the gel shown in FIG. 9 confirms the results shown in FIG. 8. The samples run in the gel included samples from both ATKA and SMB studies, and from both nanofibre IEXD and sartobind IEXD adsorbents. The Sartobind IEXD membranes did not capture all of the BSA during the loading, which is expressed by the 66 kDa band that can be seen in the flow through sample (well 6) on the gel. In contrast the flow through sample from the nanofibre adsorbent (well 4) indicates no BSA present. The same is observed in wells 9 and 10 showing the flow through from 2 Nanofibre DEAE SMB runs. Wells 7 and 8 show the product streams from 2 Nanofibre DEAE SMB runs which indicated the same result as the product stream of the separation carried out on the AKTA Basic (well 3), where BSA was present in the eluate but Cytochrome C was not. Wells 11 and 12 show the components of the product and waste streams during an SMB run using Sartobind IEXD membranes. The product stream contained only BSA but the waste stream appeared to contain both Cytochrome C and BSA suggesting that not all the BSA was being captured as seen with the AKTA Basic separation in well 6. The gel indicates that the nanofibre adsorbents performed preferentially in both the modes of operation.

Throughput and Productivity

The SMB system relies on a series of valves to switch at given time points to direct the flow of the different mobile phases. In order to optimise the performance of the system, and therefore productivity, the 18 valves must direct the different phases to different locations at exactly the right time. Once optimisation of productivity for the 2-component system was complete 200 mg BSA was repeatedly purified from the two-component protein mixture in 7.5 minutes using three column volumes of 0.15 mL implying an overall system productivity of 1.72 g/hour. This relates to a system productivity of 3.92 g (product)/mL (adsorbent)/hour.

| Adsorbent | Dynamic Binding Capacity (mg/mL) | Operating Flowrate (CV/h) | Operating Flowrate (cm/h) | Productivity (g/mL/h) |
|---|---|---|---|---|
| Nano-DEAE | 10 | 12000 | 360 | 3.92 |
| Sarto-IEXD | 6.5 | 6000 | 180 | 1.22 |
| DEAE Sepharose | 110 | 24 | 60 | 0.1 |

Table 1 shows data comparing the average productivities of the DEAE nanofibre adsorbents and the Sartobind IEXD achieved during SMB operation. Operational flow rates were chosen to maintain a standard pressure drop of 0.125 bar across the different adsorbents. Productivity calculations (expressed as Grams of product per Millilitre of adsorbent per Hour) were based on the following column dimensions: Porous beaded system 0.7 × 2.5 cm (W × H), other adsorbents 2.5 × 0.204 cm (W × H).

Data collected by the three SMB UV sensors is shown in the chromatogram of FIG. 10. The signal created by the sensors was fed back into the NI analogue input module and recorded by a Labview program that was specifically written for this purpose. The traces show how all three adsorbent columns operated similarly and how the different phases ran through each column at a particular time. The flow through was observed as the smaller peak containing Cytochrome C and the larger elution peak containing the target molecule, BSA. The high level of consistency observed highlights the suitability of these nanofibre adsorbents for operation in continuous processing applications.

The productivity that was achieved was limited by the simple design of the SMB system which utilised only three adsorbent modules in sequence and could only be run at 360 cm/h due to the limitations of the SMB system. Productivity calculations were based on chromatography cycle times for the loading, washing, elution, and regeneration of the adsorbents for set flow rates. Using the productivity ratios that were established at the SMB system's limits productivities for higher flow rates were extrapolated based on the known pressure drop limitations of each type of adsorbent. In a previous study it was shown that the nanofiber adsorbents could operate at a flowrate of 2,400 cm/h with a pressure drop across the adsorbent of less than 0.5 bar [31]. For the DEAE Sepharose comparison phase lengths were taken from recommended values in literature [42].

| Adsorbent | Dynamic Binding Capacity (mg/mL) | Operating Flowrate (CV/h) | Operating Flowrate (cm/h) | Calculated Productivity (g/mL/h) |
|---|---|---|---|---|
| Nano-DEAE | 10 (± 0.3) | 80000 | 2,400 | 26 |
| Sarto-IEXD | 6.5 (± 0.71) | 40000 | 1,200 | 5 |
| DEAE Sepharose | 110 | 150 | 375 | 0.6 |

Table 2 shows data comparing the potential productivity of the adsorbents operating at their maximum established flow rate for a pressure drop of 0.5 bar. Productivity calculations (expressed as Grams of product per Millilitre of adsorbent per Hour) were based on the following column dimensions: Porous beaded system 0.7 × 2.5 cm (W × H), other adsorbents 2.5 × 0.204 cm (W × H).

Flow Distribution

To facilitate suitable flow distribution of media through these adsorbent materials a bespoke adsorbent holder was machined. In addition to this suitable packing of the adsorbent into bespoke adsorbent holders is required to promote flow distribution. To evaluate flow distribution, a dye solution (Coomassie Brilliant Blue dissolved in 20 mM Bis-Tris buffer, pH 5.8) was loaded onto the adsorbent.

After loading with a dye solution the adsorbent holder was disassembled to show the suitable coverage of the flow showing even flow distribution. FIG. 11 shows the photographs of the adsorbents after the dye flow distribution study which utilised 3 different stainless steel frits containing different pore sizes. The formation of air bubbles underneath the frit also presented an issue for flow distribution but these would be removed by flowing 20% ethanol through the packed bed prior to normal operation.

The photographs from the flow distribution study shown in FIG. 11 demonstrate the requirement for creating distribution prior to loading onto these adsorbents. A 5 μm stainless steel frit offered the most even distribution that would be required to utilise the adsorbents to their maximum efficiency. The removal of air bubbles underneath the frit is also required by the flow through of 20% ethanol prior to normal operation.

REFERENCES

[1] June 2011, World Preview 2016, EvaluatePharma.com
[2] Reichert, J. M. 2004. Biopharmaceutical approvals in the US increase, Regul. Aff. J. Pharm. 19 (2004), p. 1

[3] Rader, R. A. 2009. BIOPHARMA: Biopharmaceutical Products in the U.S. and European Markets. Biotechnology Information Institute, Rockville, USA Available at: http://www.biopharma.com/approvals_2009.html [Accessed 11 Aug. 2011]

[4] S. Aldridge, Overcoming challenges in biomanufacturing, Genet. Eng. News 23 (2003), p. 14

[5] F. Sundberg, Coming to terms with compliance, Pharm. Technol. 15 (2003), p. 39

[6] A. C. A. Roque, C. R. Lowe and M. A. Taipa, Antibodies and genetically engineered related molecules: production and purification, Biotechnol. Prog. 20 (2004), p. 639

[7] E. N. Lightfoot and J. S. Moscariello, Bioseparations, Biotechnol. Bioeng. 87 (2004), p. 259

[8] Meir Wilchek and Talia Miron (1999). "Thirty years of affinity chromatography". Reactive and Functional Polymers 41: 263-268 Available at: http://www.wolffund.org.il/cat.asp?id=24&cat_title=MEDICINE [Accessed 11 Aug. 2011]

[9] Farid, S. S. 2006. Establishing Bioprocesses for Producing Antibodies as a Basis for Future Planning. Adv Biochemical Engineering. Biotechnology, 101, 1-42

[10] Roque, A. C. A., Taipa, M. A., Lowe, C. R. 2005. An artificial protein L for the purification of immunoglobulins and Fab fragments by affinity chromatography. Journal of Chromatography A, v 1064, n 2, p 157-167

[11] Cossins, A. J., Harrison, S., Popplewell, A. G., Gore, M. G. 2006. Recombinant production of a VL single domain antibody in *Escherichia coli* and analysis of its interaction with peptostreptococcal protein L. Protein Expression and Purification, 51, 253-259

[12] P. R. Levison, Large scale ion-exchange column chromatography of proteins: comparison of different formats, J. Chromatogr. B 790 (2003), p. 17

[13] R. Ghosh, Protein separation using membrane chromatography: opportunities and challenges, J. Chromatogr. A 952 (2002), p. 13

[14] C. Charcosset, Purification of proteins by membrane chromatography, J. Chem. Technol. Biotechnol. 71 (1998), p. 95

[15] M. Phillips, J. Cormier, J. Ferrence, C. Dowd, R. Kiss, H. Lutz and J. Carter, Performance of a membrane adsorber for trace impurity removal in biotechnology manufacturing, J. Chromatogr. A 1078 (2005), p. 74

[16] X. Zeng, E. Ruckestein, Ind. Eng. Chem. Res. 35 (1996) m 4169

[17] A. Tejeda, J. Ortega, I. Magana and R. Guzman, Optimal design of affinity membrane chromatographic columns, J. Chromatogr. A 830 (1999), p. 293

[18] M. Weissenborn, B. Hutter, M. Singh, T. C. Beeskow, F. B. Anspach, Biotechnol. Appl. Biochem. 25 (1997) 159

[19] M. B. Tennikov, N. V. Gazdina, T. B. Tennikova and F. Svec, Effect of porous structure of macroporous polymer supports on resolution in high-performance membrane chromatography of proteins, J. Chromatogr. A 798 (1998), p. 55

[20] F. T. Sarfert and M. R. Etzel, Mass transfer limitations in protein separations using ion-exchange membranes, J. Chromatogr. A 764 (1997), p. 3

[21] B. Kalbfuss, M. Wolff, L. Geisler, A. Tappe, R. Wickramasinghe, V. Thom and U. Reichl, Direct capture of influenza A virus from cell culture supernatant with Sartobind anion-exchange membrane adsorbers, J. Membr. Sci. 299 (2007), p. 251

[22] J. X. Zhou, T. Tressel, Basic Concepts in Q Membrane Chromatography for Large-Scale Antibody Production, Biotechnol. Prog. 22 (2006) 341-349

[23] M. B. Tennikov, N. V. Gazdina, T. B. Tennikova, F. Svec, Effect of porous structure of macroporous polymer supports on resolution in high-performance membrane chromatography of proteins, J. Chromatogr. A 798 (1998) 55

[24] Sartobind Membranes, Sartorius Stedim Biotech S.A., Aubagne Cedex, France

[25] Mustang Membrane, Pall Life Sciences, Portsmouth, United Kingdom

[26] ChromaSorb™ Membrane Adsorber, Millipore UK Ltd, Co Durham, United Kingdom

[27] Z. Ma, M. Kotaki and S. Ramakrishna, Electrospun cellulose nanofiber as affinity membrane, J. Membr. Sci. 265 (2005), p. 115

[28] Z. Ma, Z. Lan, T. Matsurra, and S. Ramakrishna, Electrospun polyethersulfone affinity membrane: Membrane preparation and performance evaluation, J. Chromatogr. B 877 (2008), p. 3686

[29] L. Zhang, T. J. Menkhaus and H. Fong, Fabrication and bioseparation studies of adsorptive membranes/felts made from electrospun cellulose acetate nanofibers, J. Membr. Sci. 319 (2008) p. 176

[30] W. Shi, F. Zhang and G. Zhang, Mathematical analysis of affinity membrane chromatography, J. Chromatogr. A 1081 (2005), p. 156

[31] O. Hardick, B. Stevens and D. G. Bracewell, Nanofibre fabrication in a temperature and humidity controlled environment for improved fibre consistency, J. Mater. Sci. 46 (2011) p. 3890

[32] D. M. Ruthven and C. B. Ching, *Chem. Eng. Sci.* 44 (1989), p. 1011

[33] M. Schulte and J. Strube, *J. Chromatogr. A* 906 (2001), p. 399

[34] D. W. Guest, Evaluation of simulated moving bed chromatography for pharmaceutical process development, J. Chromatogr. A 760 (1997), pp. 159-162

[35] R. Nicoud and R. Majors, Simulated moving bed chromatography for preparative separations, LC-GC 18 (7) (2000), p. 680

[36] Subramanian, G. (Ed.), 2007. Bioseparation and Bioprocessing, Volume 1: Germany: Wiley-VCH. P. 235

[37] G. Ströhlein, L. Aumann, T. Müller-Späth, A. Tarafder and M. Morbidelli, Continuous Processing: The Multicolumn Countercurrent Solvent Gradient Purification Process: A continuous chromatographic process for monoclonal antibodies without using Protein A, biopharm international, Feb. 2, 2007. Available at: http://biopharminternational.findpharma.com/biopharm/article/articleDetail.jsp?id=401628&sk=&date=&pageID=3 [Accessed 11 Aug. 2011]

[38] L. Aumann, and M. Morbidelli, A Continuous Multicolumn Countercurrent Solvent Gradient Purification (MCSGP) Process, Biotechnology and Bioengineering, 98 (2007), p. 1043

[39] M. R. Bilad, P. Westbroek, I. Vankelecom, Assessment and optimization of electrospun nanofiber-membranes in a membrane bioreactor (MBR), J. Mem. Sci 380 (2011) p. 181

[40] S. Kaur, Z. Ma, R. Gopal, G. Singh, S. Ramakrishna, T. Matsuura, Plasma-induced graft copolymerization of poly(methacrylic acid) on electrospun poly(vinylidene fluoride) nanofiber membrane, Langmuir 23 (2007) p. 13085

[41] M. Ziabari, V. Mottaghitalab, A. Haghi, Evaluation of electrospun nanofiber pore structure parameters, Korean J. Chem. Eng., 25 (2008) p. 923

[42] O. Hardick, S. Dods, B. Stevens and D. G. Bracewell, Nanofiber Adsorbents for High Productivity Downstream Processing, Biotechnology and Bioengineering (2012) doi: 10.1002/bit.24765.

[43] Hahn R, Panzer M, Hansen E, Mollerup J, Jungbauer A. 2002. Mass transfer properties of monoliths. Sep Sci Technol 37(7): 1545-1565.

The invention claimed is:

1. A chromatography medium comprising one or more electrospun polymer nanofibres wherein the electrospun cellulose nanofibers are fused together at points where the nanofibers intersect one another, and which in use form a stationary phase comprising a plurality of pores through which a mobile phase can permeate, and wherein the chromatography medium has anion exchange surface functionality interactive with target molecules.

2. The medium according to claim 1, wherein the stationary phase is in the form of a membrane.

3. The medium according to claim 2, wherein the membrane has a thickness of 100 µm to 1 mm.

4. The medium according to claim 1, wherein the nanofibres are non-woven nanofibres.

5. The medium according to claim 1, wherein the polymer is selected from: nylon, poly(acrylic acid), polyacrylonitrile, polystyrene and polyethylene oxide.

6. The medium according to claim 1, wherein the polymer is cellulose.

7. The medium according to claim 1, wherein the polymer nanofibres may be covalently cross-linked.

8. The medium according to claim 1, wherein the nanofibres have a diameter of 10 nm to 1000 nm.

9. The medium according to claim 1, wherein the nanofibres have a diameter of 200 nm to 800 nm.

10. The medium according to claim 1, wherein the nanofibres have a diameter of 300 nm to 400 nm.

11. The medium according to claim 1, wherein the mean length of nanofibres is greater than 10 cm.

12. The medium according to claim 1, wherein the pores have a diameter of 10 nm to 10 µm.

13. The medium according to claim 12, wherein the pores have a narrow size distribution.

14. A chromatography method using the medium according to claim 1.

15. The method according to claim 14, wherein the chromatography is ion exchange chromatography.

16. The method according to claim 15, wherein the chromatography is affinity capture chromatography.

17. The method according to claim 14, wherein the medium is used to isolate biological molecules from the mobile phase.

18. The method according to claim 17, wherein the biological molecules have a molecular weight of 1 kDa to 200 kDa.

19. The method according to claim 17, wherein the biological molecules have a molecular weight of 10 kDa to 100 kDa.

20. The method according to claim 18 or 19, wherein the biological molecules are selected from the group comprising: recombinant proteins, monoclonal antibodies, viral vaccines and plasmid DNA.

21. The method according to claim 15, wherein a simulated moving bedsystem is employed.

22. A cartridge for use in chromatography comprising:
two or more membranes including the medium according to claim 2 arranged in series; and
a holding member to fix the membranes in place relative to one another.

* * * * *